United States Patent [19]

Freeman

[11] 4,416,288

[45] Nov. 22, 1983

[54] APPARATUS AND METHOD FOR RECONSTRUCTING SUBSURFACE ELECTROPHYSIOLOGICAL PATTERNS

[75] Inventor: Walter J. Freeman, Berkeley, Calif.

[73] Assignee: The Regents of the University of California, Berkeley, Calif.

[21] Appl. No.: 178,170

[22] Filed: Aug. 14, 1980

[51] Int. Cl.³ .............................................. A61B 5/04
[52] U.S. Cl. .................................... 128/731; 364/417
[58] Field of Search ............................... 128/639–640, 128/644, 653, 696, 709–710, 731–732, 734; 364/415, 417, 728, 819–824

[56] References Cited

U.S. PATENT DOCUMENTS

| | | | |
|---|---|---|---|
| 3,442,264 | 5/1969 | Levitt | 128/712 |
| 3,516,400 | 6/1970 | Krohn et al. | 128/696 |
| 3,841,309 | 10/1974 | Salter et al. | 128/731 |
| 4,201,224 | 5/1980 | John | 128/731 |
| 4,214,591 | 7/1980 | Sato et al. | 128/731 |
| 4,249,538 | 2/1981 | Musha et al. | 128/639 |
| 4,263,920 | 4/1981 | Tasto et al. | 128/734 |
| 4,275,743 | 6/1981 | Hjort | 128/731 |

OTHER PUBLICATIONS

Alpers, B. J. et al., "Essentials of the Neurological Examination", F. A. Davis Co., Philadelphia Pa. 1971, p. 53.
Ueno, S. et al., "Topographic Computer Display of Abnormol EEG Activities in Patients W/CNS Diseases", Memories Foc. of Energy, Kyushu University, vol. 34, No. 3, Feb. 1975.
Freeman, Abstract Titled, "Cinematic Display of Spatial Structure of EEG and Average Evoked Potentials (AEPs) of Olfactory Bulb and Cortex", Jun. 15–16, 1973.
Freeman, "Spatial Frequency Analysis of an EEG Event in the Olfactory Bulb", Continued in the Work Entitled, Multidisciplinary Perspectives in Event-Related Brain Potential Research, Dec., 1978.
Freeman, Abstract, titled, "A Software Lens for Image Reconstitution of the EEG", May, 1979.

Primary Examiner—Kyle L. Howell
Assistant Examiner—Francis J. Jaworski
Attorney, Agent, or Firm—Fitch, Even, Tabin, & Flannery

[57] ABSTRACT

Signals representative of electric potentials generated by cells of a given depth in the cerebral cortex or in other organs of a living body are detected at the surface thereof by an array of electrodes. These signals are amplified, digitized, and then spatially deconvoluted, to remove distortions introduced by the physical properties of the organ, to recover the desired pattern of electric potential within the living body.

14 Claims, 3 Drawing Figures

APPARATUS AND METHOD FOR RECONSTRUCTING SUBSURFACE ELECTROPHYSIOLOGICAL PATTERNS

The invention described herein was made in the course of, or under a grant from the National Institute of Mental Health.

This invention relates in general to a method and apparatus for analyzing electrophysiological signals which have been generated by a living subject, and more particularly to a method and apparatus for reconstructing a pattern of electrical activity within the living body from the signals detected at the surface thereof by spatially deconvoluting these surface signals.

Prior art devices for detecting and displaying electrical activity in living organisms have had many drawbacks. A basic electroencephalograph (EEG), for example, can only detect an analog signal on the surface of the brain. It usually transmits this signal to a recorder for readout on a strip chart or the like. Such a record provides only a very gross summary indication of the complex electrical activity actually being generated by the brain.

More recently, closed spaced arrays of electrodes have been used in an attempt to observe variations in the electric field potential of an area or region of the brain or other organ. The drawback of these latter devices has been that the potential detected at any one point is still the sum of the potential created by an indefinitely large number of electric potential generators in the surrounding area. Thus, the image received is distorted, a distortion which is introduced by the physical properties of the generators. This distortion results in a smoothing or smearing of the image, which is equivalent to the blurring which occurs in a photograph when it is out of focus.

The present invention is directed towards mathematically defining this blurring function through knowledge of the physical characteristics of the organ and its electric potential generators. An inverse of this function is then generated and used to modify the electric potentials measured on the surface, to refocus or reconstruct a more accurate image of the subsurface electric potential pattern.

More specifically, when an EEG detects the amplitude of a point on the surface of the cerebral cortex, for example, what is detected is the overlapping summation of electic fields generated by active neurons in the depths of the cerebral cortex, which have spread through the tissues and up to the surface. These nerve cells can be characterized as point dipoles which are oriented perpendicular to the surface of the cerebral cortex. In other words, each cell has a current source where positive charge moves outwardly across its membrane and a current sink where the same amount of positive charge moves inwardly at each instant. Thus, the flow of current across each cell establishes an electric field potential that is equivalent to the electrostatic field potential of a pair of point charges, one positive at the location of the current source and one negative at the current sink. The key element is that the amplitude of this field potential, i.e., the electic field strength, decreases inversely with distance in all directions from each point charge, and is relatively low at the surface of the cerebral cortex.

When many nerve cells are generating the above described field potentials in a given region, these potentials sum and overlap in the tissue, in the extracellular fluid, and at the brain surface. This summation is a linear function in this volume conductor, since as mentioned above, the field strength of a given cell varies inversely as a function of the distance from each current source or sink. Thus, if the electic potential of a given region is measured at a sufficient number of points, it is possible to deduce the locations and amplitude of each dipole generator at any instant of time.

The above described process is facilitated in the cerebral cortex, as in certain other organs, where the nerve cells have a regular geometry, forming a sheet of point dipoles at a specific depth below the surface of the cortex. Consequently, this summation process, i.e. the distortion in the electric field pattern of the cells resulting from the number of spaced apart generators being conducted through the tissue volume, can be described by the mathematical operation of convolution. The standard manner of spread is called the kernel or point spread function. A pattern of neural activity within the cortex can be said to be convolved with the kernel to give the surface EEG pattern.

When this kernel is known, its inverse may be computed. Then convolution of a surface EEG pattern with this inverse kernel should restore the original neural activity pattern. This procedure is termed spatial deconvolution of the EEG.

Therefore, an object of the present invention is to provide an apparatus and method for reversing the smearing of blurring distortions created in an electric potential pattern caused by the volume conduction of a tissue.

Another object of the present invention is to provide an apparatus and method for enhancing cerebral electrical signals detected by an array of electrodes attached to the surface of the head of a living body.

A further object of the present invention is to provide an apparatus and method for enhancing electrophysiological signals, wherein the steps of sampling and analyzing said signals is performed at a fast enough rate to enable real time viewing of changes in the electric field potential patterns.

These and other objects and advantages of the present invention will become more apparent upon reference to the following description and accompanying drawings, wherein.

Figure 1:
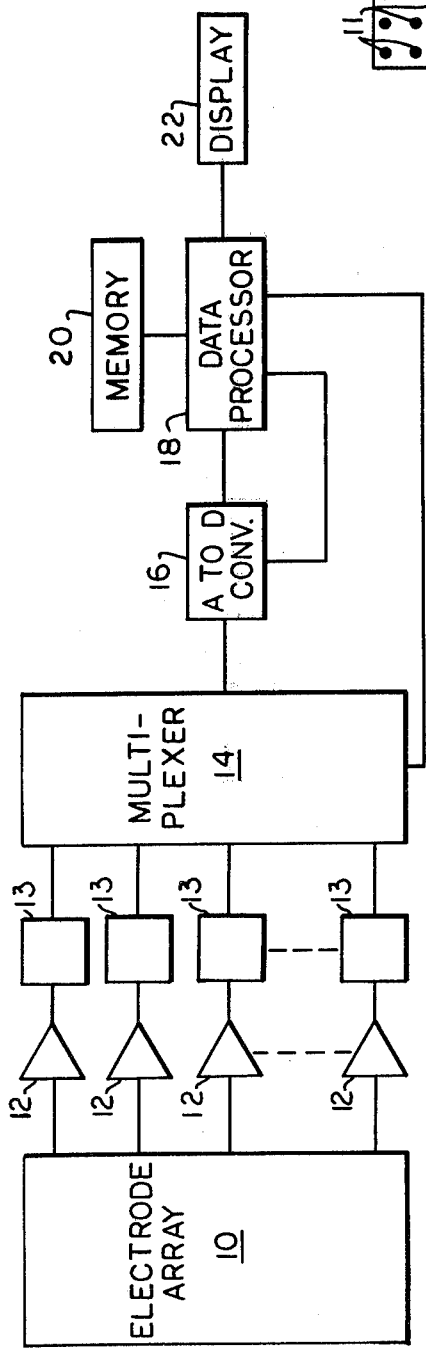
FIG. 1 is a block diagram of an apparatus according to the present invention.

Referring now to FIG. 1, an electrode array 10 is most simply a rectangular array of discrete electrodes. As will be seen hereinbelow, a rectangular or square arrangement of electrodes facilitates (but is not essential for) the spatial deconvolution steps described herein required to reconstruct the underlying electrophysiological patterns from the detected surface signals. The spacing between adjacent electrodes should be equal, and of an amount dictated by the maximum spatial frequency, or spatial rate of change, of the electric field potential being detected. That is, the optimal spacing between electrodes is determined by the expected spatial frequency of the signals being detected. Provided the inter-electrode spacings are less than half the shortest spatial wavelength to be encountered, the arrangement may be irregular, if the placements are all measured with respect to a common spatial reference point on the surface.

Figure 2:
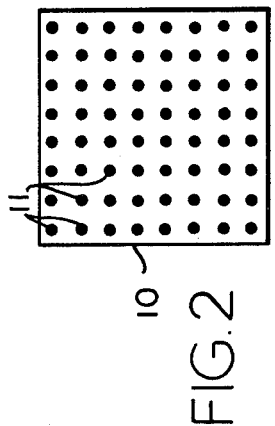
FIG. 2 is a plan view of one embodiment of an 8×8 electrode array according to the present invention.

The diameter of each electrode should be as large as possible consistent with arranging the electrodes in the desired geometric configuration, while maintaining an effective amount of insulation between adjacent electrodes. An exemplary electrode array of 8×8 or 64 electrodes is illustrated in FIG. 2.

The apparatus according to the present invention is designed to sample each of the electrodes in the electrode array 10 to measure the electric potential detected by each electrode often enough with respect to the temporal rate of change or frequency of the electric field potential being measured to ensure that an accurate amplitude is obtained. That is, if a brain wave pattern having a frequency varying between 40–100 hertz is to be measured, each electrode should be accessed at least once every 5–10 milliseconds. Basically, sampling at least once each half cycle is the minimum needed to obtain an accurate measure of the amplitude and rate of change of the electric field potential being detected by a given electrode. It should be noted that there is very little if any cerebral brain wave activity above 100 hertz. The typical regions of greatest interest are in the alpha range of 8–12 hertz, the delta range of 4–7 hertz, the beta range of 5–35 hertz, and a gamma range of 35–100 hertz.

Referring again to FIG. 1, the signal detected by each electrode is output to a separate preamplifier means 12.

The signal detected by each electrode typically varies in amplitude in the range of 10–500 microvolts. Each preamplifier means 12 is designed to provide high gain amplification for this signal, a gain of 10,000 is typical, while providing a very high input impedance and low current loading on each electrode. Low noise amplifiers are also preferred.

The preamplifier means 12 may also be used as a band pass filter to enable only that band of frequencies of interest to be further analyzed by the apparatus. A separate band pass filter means 13 may alternately be used, positioned in the signal path as shown in FIG. 1. Other conventional types of band pass filtering are also contemplated as being within the scope of the present invention.

The signal output from each of the preamplifier means 12 and band pass filter means 13 are coupled to a multiplexer 14. Multiplexer 14 acts to sequentially sample each of its plurality of inputs, corresponding to a separate amplified and filtered analog signal from each electrode 11, and to output a time division multiplexed signal as a function of these inputs. This output is coupled to an analog to digital convertor 16. Convertor 16 outputs a separate 12 bit digital word for each electrode 11, whose bit state represents the amplitude of the given signal detected by that electrode 11. Each electrode in the array is sampled and its output digitized, by the convertor 16 before this sampling process is repeated.

In an embodiment having an electrode array of 8×8 electrodes, a total of 64 EEG electrodes, for example, the conversion of all 64 analog sampled electrode signal amplitudes would be performed in a period of 0.640 milliseconds if each electrode is sampled and its signal digitalized every 10 microseconds. This rate enables convenient sampling of electric field potentials varying at a rate of up to 100 hertz.

The output of analog digital convertor 16 is fed to a data processor 18. Data processor 18 analyzes the sampled digitized signals representing a given event at a particular point in time, and either stores this data in a memory 20 or displays it in a conventional display 22. Display 22 may be a conventional contour plot generator apparatus, a CRT display, or the like.

Note that the data processor 18 can be used to immediately calculate the spatial deconvolution transformation of the detected electrode field potentials. Alternatively, the data can be initially checked for artifacts, and if no artifacts are found, then the event is analyzed. Artifacts would include erroneous signals resulting from movement of the animal being measured, cable noise, or wherein a specific electrode or electrodes fail. In this latter example, the signal detected by a specific electrode can be eliminated under computer program control, enabling the rest of the sampled amplitudes from the other electrodes in array 10 to be retained for further analysis.

The data processor 18 may also provide conventional controller means for the multiplexer 14 and analog to digital convertor 16 to insure that convertor 16 samples and digitizes an analog signal at an appropriate rate, and that the analog signal from each electrode 11 is thereby separately and accurately digitized into a 12 bit word.

Figure 3:
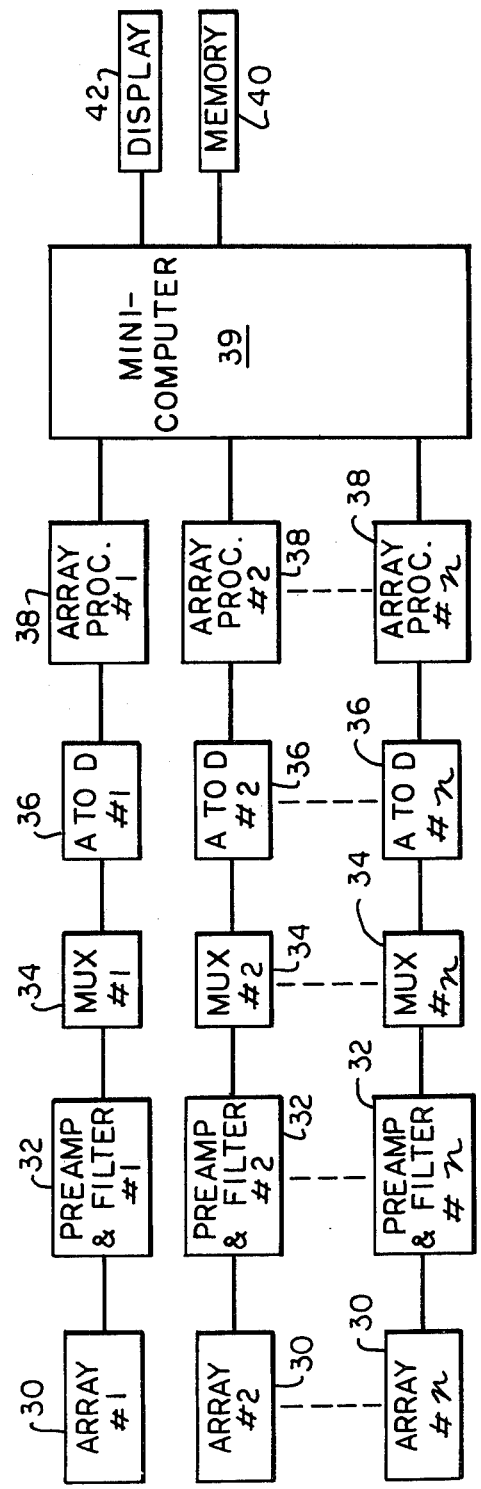
FIG. 3 is a block diagram of a second preferred embodiment of the present invention.

FIG. 3 is an alternate preferred embodiment of the present invention, wherein a plurality of electrode arrays 30 are defined, e.g. electrode array 30 #'s 1-N, with each electrode array feeding a separate block of preamplifiers and band pass filters 32. Each block of preamplifiers 32 would then feed a separate multiplexer 34, whose output is fed to an analog to digital (A to D) convertor 36. The output of each A to D convertor 36 is fed to a processor 38. A useful configuration is to place the analog to digital converter 36 and multiplexer 34 under the direct control of an array processor, which is in turn controlled by a minicomputer 39. After each multiplexer 34 scan of the array of preamplifiers. the array processor 38 deconvolutes the spatial frame, and the data are transferred to the minicomputer as a new frame is read. Microprocessor 39 would also have access to a conventional memory 40 and display 42.

One advantage of this alternate embodiment would be the elimination of any time constrains created in the system resulting from slowness in the A to D conversion process, a process which normally takes a fixed period of time to accomplish for each analog signal sampled. The embodiment of FIG. 3 also illustrates a convenient manner of expanding the system without a substantial increase in operating complexity.

Specifically referring now to the computations involved in analyzing the sampled data obtained by the data processor, there exists at a given instant of time + a pattern of cell generated electric field potential activity U at a depth $z=z_o$ in the organ being observed, having coordinates x', y', and describeable as the function $U(x', y', t)$. This activity gives rise to a pattern of EEG activity V at the surface of the cortex at coordinates x, y, describeable as the function $V(x,y,t)$. A transformation function $f_z(x-x', y-y')$ of U into V is determined by the laws of conduction in the volume.

In order to simplify the formation of this transform $f_z$, the following assumptions can be made, using the cerebral cortex as an example.

(a) Each active subset of cells of neurons under a given surface electrode can be represented by an axially symmetric dipole current generator oriented perpendicular to the surface of the cortex.

(b) The amplitude of the dipole can be represented by the amplitude of an equivalent pair of negative and positive point charges separated by a distance $2\lambda$.

(c) The set of active cells forms a homogeneous layer oriented parallel to the surface at a depth z.

(d) The array of electrodes at the surface is parallel to this subsurface layer of cells, with inter-electrode distance equal to $\Delta x \Delta y$.

(e) The potential at the surface is measured essentially simultaneously at each time t for all electrodes.

Using the above simplifying assumptions, the convolution transformation of neural activity U at a depth V to give the EEG activity V by volume conduction is:

$$V(x, y, t) = \sum^{x'} \sum^{y'} f_z(x - x', y - y') u(x', y', t) \Delta x' \Delta y', \quad (1)$$

where:

$$f_z(x - x', y - y') = \frac{(a_1 - a_2)}{a_0} \quad (2)$$

This latter equation reflects the fact that for each point source and point sink, the field strength falls off as a function of the inverse of the distance. Normalizing this equation for an amplitude epicenter at $x=0$ and $y=0$, to eliminate the need for a parameter to reflect the conductance of the tissue, the following values for $a_0$, $a_1$ and $a_2$ are derived:

$$a_1 = [(x-x')^2 + (y-y')^2 + (z_0+\lambda)^2]^{-0.5}$$

$$a_2 = [(x-x')^2 + (y-y')^2 + (z_0-\lambda)^2]^{-0.5}$$

$$a_0 = [x^2+y^2+(z_0+\lambda)^2]^{31}$$
$$0.5 - [x^2+y^2+(z_0-\lambda)^2]^{-0.5} \quad (3)$$

For a specific number of electrode recording sites N, the U and V patterns can be expressed as $(N \times 1)$ column vectors $U(t)$ and $V(t)$, and the $f_z$ transform as an $(N \times N)$ matrix $F_z$. The convolution operation in the cortex is then approximated by matrix multiplication as follows:

$$V(t) = F_z U(t) \quad (4)$$

Deconvolution to recover the desired subsurface pattern of electrical potential $U(t)$ from the EEG samples is given by: $U(t) = F_z^{-1} V(t)$.

Thus, the subsurface pattern $U(t)$ can be obtained by multiplying the inverse matrix $F_z^{-1}$ by the samples obtained at the surface by the EEG.

Thus, for example, if an $8 \times 8$ electrode array were being used, the size of the transform matrix would be $64 \times 64$, and the column vectors $U(t)$ and $V(t)$ would each be $64 \times 1$ matrices. Consequently, once the above described transformation using the inverse matrix $F_z$ is completed, the column vector $U(t)$ contains 64 separate values which can be easily reassembled as the enhanced $8 \times 8$ array for output to a contour plot generator, or some other display 22, of this enhanced pattern.

The above calculations would be more complex if the impedance characteristics of the tissue in which volume conduction takes place are significantly non-unifom or anisotropic. That is, if the value of the resistivity of the medium is not approximately the same throughout the spatial distribution of the array, or if the value of the impedance in different directions with respect to the surface is significantly non-uniform, then a series of distortions can result. To compensate for such distortions, it would be necessary to use tensor analysis to describe the relationship between this activity and the observed field potentials at the surface of the organ. It has been found, however, that this degree of departure from homogeneity and anisotropisity is less than 4 or 5% and can therefore be considered negligible.

Another aspect which would make these calculations more complex is if the capacitive effects of the tissue were considered. These effects would be inverse hyperbolic functions of the applied potential frequency. It has been found, however, that this degree of departure from homogeneity is also small, since the magnitude of the reactance vector component is again only on the order of a 4 or 5% effect, and can therefore be considered negligible.

It is of course understood that although the preferred embodiments of the present invention have been illustrated and described, various modifications, alternatives and equivalents thereof will become apparent to those skilled in the art, and, accordingly, the scope of the present invention should be defined only by the appended claims and equivalents thereof.

What is claimed is:

1. An apparatus for recovering a pattern of cell generated electrical field potential U occurring at a specific time t and at a selected depth within a living organ from an associated pattern of electrical potential V at said specific time and at the surface of said living organ, said cell generated electrical field potential U having coordinates x', y' and being describable as $U = U(x', y', y', t)$, said electrical potential V having coordinates x, y and being describable as $V = V(x, y, t)$, said apparatus comprising:

an electrode array for detecting values of $V(x, y, t)$ at a plurality of points on the surface of said living organ, said points being spaced from each other by a distance determined by the expected spatial frequency of said electrical potential $V(x, y, t)$;

means for digitizing the detected values of $V(x, y, t)$; and means for spatially deconvolving the digitized values of $V(x, y, t)$ to recover the desired pattern of electrical field potential $U(x', y', t)$ within said living organ, said deconvolving means including computing a transform function $f_z = f_z(x-x', y-y')$, said transform function having the value determined by an equation which describes the field potential at each of a plurality of subsurface points with respect to the field potential of each of a plurality of other selected sets of subsurface electric field potential generators, such that the potential at any one point is the sum of potentials from such surrounding generator sets, with each potential having a value determined by the laws of conduction in the volume of said organ, and means for computing the product of said surface field potential $V(x, y, t)$ and the inverse of said transform function to generate values of the electric field potential $U(x', y', t)$.

2. The apparatus of claim 1 wherein said means for spatially deconvolving the digitized values of $V(x,y,t)$ comprises:

means for computing a matrix relationship between the fields of potential of each of a plurality of selected sets of subsurface electric field potential generators, such that the potential at any one point approximates the sum of potentials from an indefinite number of surrounding generator sets weighted as a function of their distance from said point; and means for computing the matrix product of V(x,y,t) and the inverse of said matrix to generate values of U(x', y', t).

3. The apparatus of claim 1 wherein said electrode array includes a plurality of electrodes spaced such that they are separated by a distance that is less than one half the shortest spatial wavelength of the detected values of V(x, y, t).

4. An apparatus for recovering a pattern of cell generated electrical field potential U occurring at a specific time t and at a selected depth within a living organ from an associated pattern of electrical potential V at said specific time and at the surface of said living organ, said cell generated electrical field potential u having coordinates x', y' and being describable as U=U(x', y', t), said electrical potential V having coordinates x, y and being describable as V=V(x, y, t), said apparatus comprising:

an array of electrodes, said array detecting an electric field potential signal at a plurality of points on the surface of said living organ, generating thereby said V(x, y, t) pattern, said points being spaced from each other by a distance determined by the expected spatial frequency of said electrical potential V(x, y, t);

amplifier means attached to each said electrode in said electrode array for amplifying said detected signal;

multiplexer means for sampling the output level of each said amplifier means and for outputting a time division multiplexed signal made up of such signal levels, said multiplexing being performed at a fast rate as compared with the rate of change of said electric field potential signals;

analog to digital converter means for digitizing said multiplexer means output;

means for controlling the operation of said multiplexer means and said analog to digital converter means, such that the output of said converter means is a plurality of digital words, each digital word reflecting the present analog level of electric field potential detected by a given electrode in said electode array; and processor means for storing said digital words until the signal outputs of each electrode in said array have been sampled and digitized, and for generating from this V(x, y, t) pattern of signals, by spatial deconvolution, a pattern of electrical potential U(x', y', t) occurring within said living organ, said spatial deconvolution being performed by computing a transform function $f_z = f_z(x-x', y-y')$, said transform function having the value determined by an equation which describes the field potential at each of a plurality of subsurface points with respect to the field potential of each of a plurality of other selected sets of subsurface electric field potential generators, such that the potential at any one point is the sum of potentials from such surrounding generator sets, with each potential having a value determined by the laws of conduction in the volume of said organ, and means for computing the product of said surface field potential V(x, y, t) and the inverse of said transform function to generate values of the electric field potential U(x', y', t).

5. The apparatus of claim 4 further comprising means for displaying said recovered pattern of electrical potential U(x', y', t).

6. The apparatus of claim 4 further comprising means for storing said patterns of electrical potential U(x', y', t) as a function of the time t of occurrence of each such pattern.

7. The apparatus of claim 4 wherein said array of electrodes comprises a rectangular array of electrodes wherein the inter-electrode spacing between adjacent electrodes is equal, and the number of electrodes in each column of said array is equal and the number of electrodes in each row of said array is equal.

8. The apparatus of claim 4 further comprising filter means for band pass filtering each said detected electric field potential signal.

9. The apparatus of claim 4 wherein said array of electrodes is arranged such that each electrode in said array is spaced such that it is separated by a distance from adjacent electrodes in said array that is less than one-half the shortest expected spatial wavelength of said detected electric field potential signal.

10. An apparatus for recovering a pattern of cell generated electrical field potential U occurring at a specific time t and at a selected depth within a living organ from an associated pattern of electrical potential V at said specific time and the surface of said living organ, said cell generated electrical field potential u having coordinates x', y' and being describable as U=U(x', y', t), said electrical potential V having coordinates x, y and being describable as V=V(x, y, t), said apparatus comprising:

a plurality of electrode arrays each detecting a separate pattern of electric field potential V(x, y, t) at a plurality of points on the surface of said living organ, said points being spaced from each other by a distance determined by the expected spatial frequency of said electrical potential V(x, y, t);

amplifier means for amplifying the signal output of each electrode in each said electrode array;

means for filtering said electric field potential signals, to eliminate frequency components therein outside of a selected band of frequency;

means for digitizing the signals output from each said electrode array;

means for spatially deconvolving the digitized signals, representing the pattern V(x, y, t) for each said electrode array, to recover the desired respective pattern of electrical potential U(x', y', t) within said living organ beneath such electrode array, said deconvolving means including computing a transform function $f_z = f_z(x-x', y-y')$, said transform function having the value determined by an equation which describes the field potential at each of a plurality of subsurface points with respect to the field potential of each of a plurality of other selected sets of subsurface electric field potential generators, such that the potential at any one point is the sum of potentials from such surrounding generator sets, with each potential having a value determined by the laws of conduction in the volume of said organ, and means for computing the product of said surface field potential V(x, y, t) and the inverse of said transform function to generate values of the electric field potential U(x', y', t).

11. An apparatus for recovering a pattern of electrical potential U(t) appearing within a living body from an associated pattern of electrical potential V(t) at the surface of said living body, comprising:

an electrode array of N insulated electrodes for detecting V(t) at a plurality of points, each corresponding to a given electrode, on the surface of said living body;

means for digitizing the detected values of V(t); and means for spatially deconvolving the digitized values of V(t) to recover the desired pattern of electrical potential U(t) within said living body, said means for spatially deconvolving comprising:

means for computing an N×N matrix having values determined by linear simultaneous equations which describe the field potential at each of a plurality of subsurface points with respect to the field potential of each of a plurality of other selected sets of subsurface electric field potential generators, such that the potential at any one point is the sum of potentials from such surrounding generator sets, with each potential having a value inversely related to its distance from such point; and means for computing the matrix product of V(t) as an N×1 column vector and the inverse of said N×N matrix to generate values of U(t) as an N×1 column vector.

12. A machine implemented method for digitally enhancing electrical signals detected by an array of electrodes attached to the surface of the brain or other organ of a living subject, such that the effects of volume conduction distortion of electric field potentials generated at a depth z below the surface of the subject is corrected, comprising the steps of:

digitizing the detected electrical signal from each of said electrodes;

defining a matrix of coupling coefficients wherein each coupling coefficient is derived for a given set of electric field potential generators according to the distance of that set to an indefinite number of other sets of generators in the organ;

obtaining the inverse of said matrix;

computing the matrix product of said inverse matrix and said digitized electrical signals in the form of a column vector; and reassembling the resultant column vector as an array of spatially deconvolved signals to obtain the desired enhanced pattern of electrical signals.

13. The method of claim 12 wherein the coupling coefficients comprise linear simultaneous equations and wherein the amplitude of potential at a given point contributed by each of the other electric field potential generator sets falls off as a function of the inverse of the distance of each such other set from said given point.

14. A machine implemented method for digitally recovering a pattern of enhanced all generated electric field potential U having coordinates x', y' as describable as U=U(x', y', t) and being detected by an array of N electrodes attached to the surface of the brain or other organ of a living subject, said electrodes detecting electrical signal V having coordinates x', y' and describable as V=V(x, y, t), such that said enhanced signals U(x', y', t) correspond to electric field potentials generated by cell generators acting as dipoles at a depth $z_0$ below the surface of the organ, where the positive and negative point charges in said dipoles are separated by the distance 2, with the effects of volume conduction distortion caused by the organ tissue being eliminated, comprising the steps of:

digitizing the detected electrical signal from each of said electrodes;

computing an N×N matrix $F_z$ of coupling coefficients wherein:

$$V(x, y, t) = \sum^{x' y'} f_z(x - x', y - y') u(x', y', t) x' y',$$

$$f_z(x - x', y - y') = \frac{(a_1 - a_2)}{a_o}$$

$a_1 = [(x - x')^2 + (y - y')^2 + (z_o + )^2]^{-.5}$
$a_2 = [(x - x')^2 + (y - y')^2 + (z_o - )^2]^{-.5}$
$a_o = [x^2 + y^2 + (z_o + )^2]^{-.5} - [x^2 + y^2 + (z_o - )^2]^{-.5}$ obtaining the inverse of said matrix, $F_z^{-1}$;

assembling the values V(x, y, t) as an N×1 column vector;

computing $U(N \times 1) = F_z - V(N \times 1)$; and reassembling the resultant column vector U(N×1) as an array of spatially deconvolved signals to obtain the desired enhanced pattern of electrical signals U(x', y', t).

* * * * *

UNITED STATES PATENT AND TRADEMARK OFFICE
CERTIFICATE OF CORRECTION

PATENT NO. : 4,416,288
DATED : November 22, 1983
INVENTOR(S) : Walter J. Freeman It is certified that error appears in the above-identified patent and that said Letters Patent is hereby corrected as shown below:

Column 1, line 25, change "closed" to --closely--.

Column 1, line 51, change "tissues" to --tissue--.

Column 2, line 30, change "of" to --or--.

Column 4, line 43, change "constrains" to --constraints--.

Column 4, line 53, change "+" to --t--.

Column 5, line 34, change the following formula:

"$a_o = [x^2 + y^2 + (z_o + \lambda)^2]^{31}$
$0.5 - [x^2 + y^2 + (z_o - \lambda)^2]^{-0.5}$"

to read as follows:

--$a_o = [x^2 + y^2 (z_o + \lambda)^2]^{-.5} - [x^2 + y^2 + (z_o - \lambda)^2]^{-.5}$--.

Column 6, line 30, change "U=U(x',y',y',t)" to
----U=U(x',y',t)--.

Column 8, line 24, after "and" insert --at--.

UNITED STATES PATENT AND TRADEMARK OFFICE
CERTIFICATE OF CORRECTION

PATENT NO. : 4,416,288         Page 2 of 2
DATED      : November 22, 1983
INVENTOR(S): Walter J. Freeman It is certified that error appears in the above-identified patent and that said Letters Patent is hereby corrected as shown below:

Column 10, line  9, change "as" to --and--.
Column 10, line 23, change "electrods" to --electrodes--.
Column 10, line 39, change "$F_2^- V(N \times 1);$" to read as follows: --$F_2^{-1} V(N \times 1);$--.

*Signed and Sealed this*

*Second* Day of *April 1985*

[SEAL]

*Attest:*

DONALD J. QUIGG

*Attesting Officer*     *Acting Commissioner of Patents and Trademarks*